United States Patent [19]

Burk

[11] Patent Number: 5,741,810
[45] Date of Patent: Apr. 21, 1998

[54] CYCLOPENTANE HEPTAN(ENE)OIC ACID, 2- HETEROARYLALKENYL DERIVATIVES AS THERAPEUTIC AGENTS

[75] Inventor: Robert M. Burk, Laguna Beach, Calif.

[73] Assignee: Allergan, Waco, Tex.

[21] Appl. No.: 608,794

[22] Filed: Feb. 29, 1996

[51] Int. Cl.⁶ .......................... A61K 31/38; A61K 31/34; C07D 333/06; C07D 317/04
[52] U.S. Cl. .......................... 514/438; 514/443; 514/461; 514/469; 549/58; 549/78; 549/79; 549/445; 549/454
[58] Field of Search .......................... 514/530, 573, 514/438, 454, 443, 461, 469–472, 445–447, 365, 367, 370, 374.5; 549/61, 68, 70, 72, 74–79, 81, 57, 58, 49, 467, 468, 471, 429, 474, 480, 481, 483, 488, 491, 496, 498, 499, 501, 504, 505; 548/152, 190, 200, 204–5, 217, 233, 236

[56] References Cited

U.S. PATENT DOCUMENTS

| | | | |
|---|---|---|---|
| 3,845,115 | 10/1974 | Lincoln, Jr. et al. | 514/530 |
| 4,560,786 | 12/1985 | Skuballa et al. | 560/55 |
| 4,585,791 | 4/1986 | Faustini et al. | 514/471 |
| 4,994,274 | 2/1991 | Chan et al. | 424/427 |
| 5,028,624 | 7/1991 | Chan et al. | 514/530 |
| 5,034,413 | 7/1991 | Chan et al. | 514/530 |
| 5,321,128 | 6/1994 | Stjernschantz et al. | 514/530 |
| 5,446,041 | 8/1995 | Chan et al. | 514/530 |
| 5,545,665 | 8/1996 | Burk | 514/530 |

OTHER PUBLICATIONS

Greene, T.W., "Protective Groups in Organic Synthesis", pp. 10–16, 1981.
Bito, L.Z., "Prostaglandins and Related Compounds as Potential Ocular Therapeutic Agents," *Biological Protection with Prostaglandins*, Cohen, M.M., ed., Boca Raton, Fla, CRC Press, Inc., 1985, pp. 231–252.
Bito, L.Z., "Prostaglandins, Other Eicosanoids, and Their Derivatives as Potential Antiglaucoma Agents,"0 *Applied Pharmacology in the Medical Treatment of Glaucomas* Drance, S.M. and Neufeld, A.H. eds., New York, Grune & Stratton, 1984, pp. 477–505.

Nilsson, et al., "PGF$_{2\alpha}$ Increases Uveoscleral Outflow," *Invest. Ophthalmol. Vis. Sci.* (suppl), 284, 1987.

Siebold, et al., "Esterified prostaglandin shows 'potent' promise," *Prodrug* 5 3, 1989.

Bito, L.Z., "Prostaglandins, Old Concepts and New Perspectives," *Arch. Ophthalmol.* 105, 1036, 1987.

Primary Examiner—Deborah Lambkin
Attorney, Agent, or Firm—Robert J. Baran; Martin A. Voet; Howard R. Lambert

[57] ABSTRACT

The present invention provides to cyclopentane heptanoic acid, 2 heteroaryl alkyl or alkenyl derivatives which may be substituted in the 1-position with hydroxyl, alkyloxy, amino and amido groups, e.g. 1-OH cyclopentane heptanoic acid, 2 heteroarylalkenyl derivatives. In particular, these derivatives are 7-[5-hydroxy-2-(heteroatom-substituted hydroxyhydrocarbyl)-3-hydroxycyclopentyl]heptanoic or heptenoic acids and amine, amide, ether, ester and alchohol derivatives of said acids wherein one or more of said hydroxy groups are replaced with an ether group. These compounds are potent ocular hypotensive and are particularly suited for the management of glaucoma. Moreover, the compounds of this invention are smooth muscle relaxants with broad application in systemic hypertensive and pulmonary diseases; with additional application in gastrointestinal disease, reproduction, fertility, incontinence, shock, inflammation, immune regulation, disorder of bone metabolism, renal dysfunction, cancer and other hypoproliferative diseases.

13 Claims, 3 Drawing Sheets

SCHEME 1

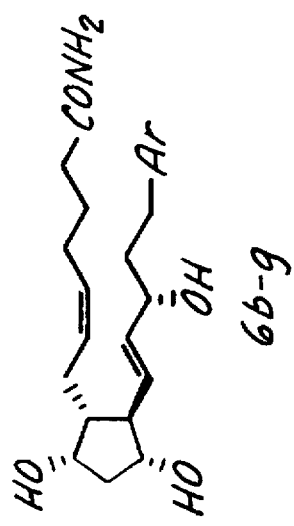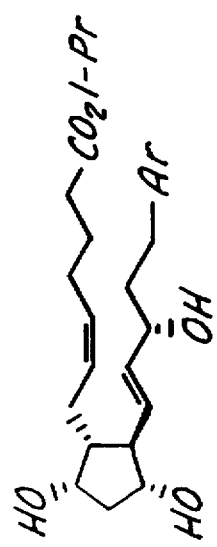
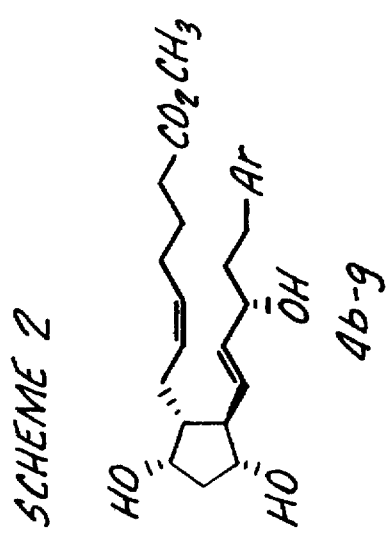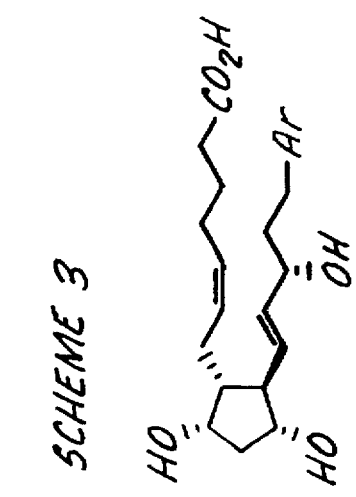
Fig. 2.
Fig. 3.

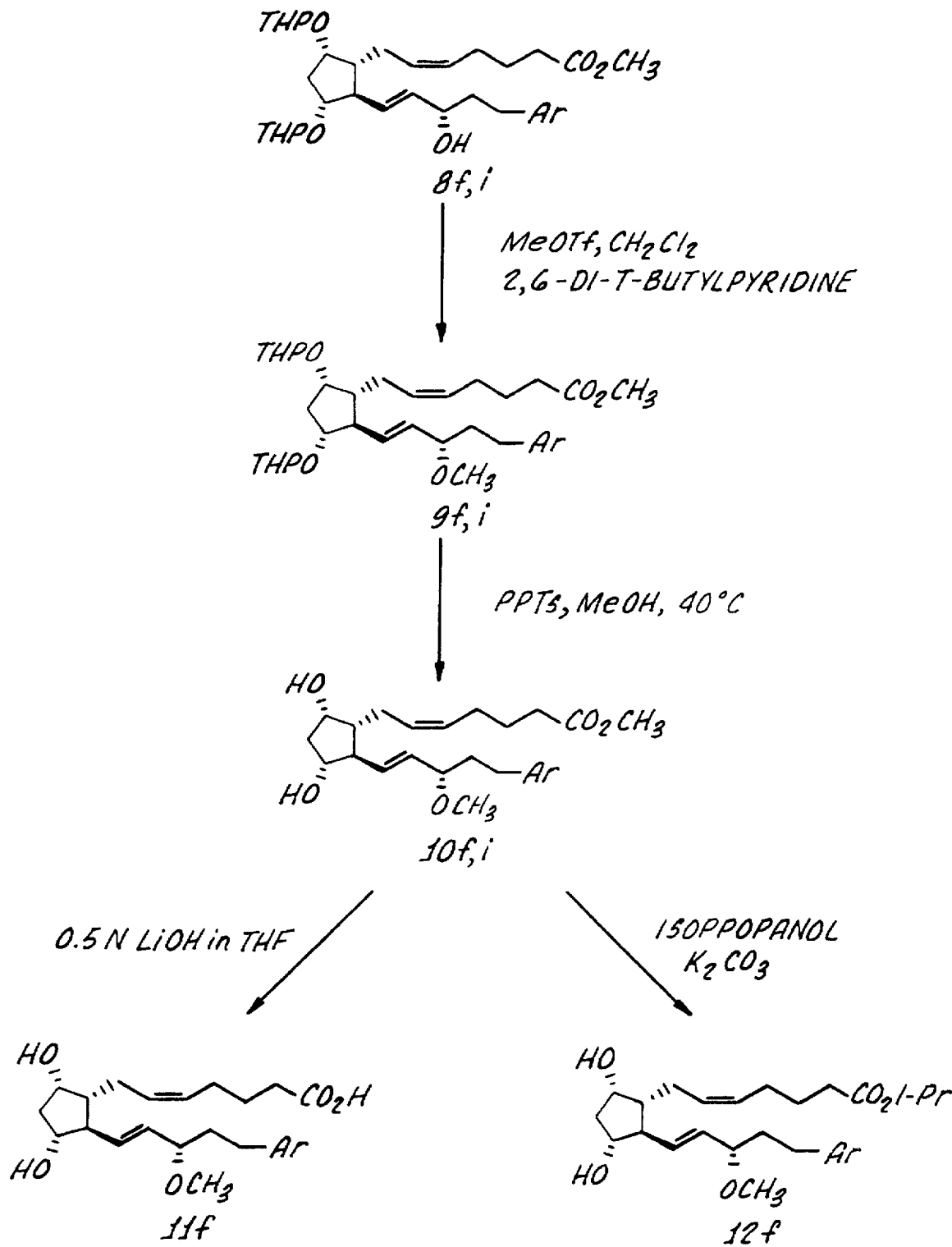

5,741,810

CYCLOPENTANE HEPTAN(ENE)OIC ACID, 2- HETEROARYLALKENYL DERIVATIVES AS THERAPEUTIC AGENTS

BACKGROUND OF THE INVENTION

1. Field of the Invention

The present invention provides cyclopentane heptanoic acid, 2 heteroaryl alkyl or alkenyl derivatives which may be substituted in the 1-position with hydroxyl, alkyloxy, amino and amido groups, e.g. 1-OH cyclopentane heptanoic acid, 2 heteroarylalkenyl derivatives. In particular, these derivatives are 7-[5-hydroxy-2-(heteroatom-substituted hydroxyhydrocarbyl)-3-hydroxycyclopentyl]heptanoic or heptenoic acids and amine, amide, ether, ester and alcohol derivatives of said acids wherein one or more of said hydroxy groups are replaced with an ether group. These compounds are potent ocular hypotensives and are particularly suited for the management of glaucoma. Moreover, the compounds of this invention are smooth muscle relaxants with broad application in systemic hypertensive and pulmonary diseases; with additional application in gastrointestinal disease, reproduction, fertility, incontinence, shock, inflammation, immune regulation, disorder of bone metabolism, renal dysfunction, cancer and other hyperproliferative diseases.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

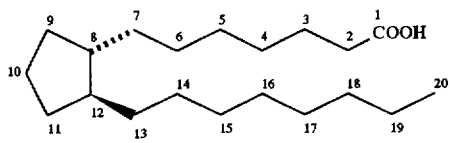

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [[e.g. prostaglandin $F_{2\alpha}(PGF_{2\alpha})$].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et. al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The copending U.S. Ser. No. 596,430 (filed 10 Oct. 1990), relates

3 to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175,476 (filed 29 Dec. 1993). Similarly, 11,15-9,15 and 9,11-diesters of prostaglandins, for example 11,15-dipivaloyl $PGF_{2\alpha}$ are known to have ocular hypotensive activity. See the co-pending patent applications U.S. Ser. Nos. 385,645 (filed 07 Jul. 1989, now U.S. Pat. No. 4,994,274), 584,370 (filed 18 Sep. 1990, now U.S. Pat. No. 5,028,624) and 585,284 (filed 18 Sep. 1990, now U.S. Pat. No. 5,034,413).

Other patents and patent applications assigned to Allergan, Inc. disclose and claim other compounds which are useful in treating increased intraocular pressure and thus are useful in the treatment of glaucoma. Said patents and patent applications include U.S. patent application Ser. No. 08/174,535, which is entitled Cyclopentane (ene) Heptenoic or Heptanoic Adds and Derivatives Thereof Useful as Therapeutic Agents and was filed on Dec. 28, 1993 and U.S. patent application Ser. No. 08/443,992, which is entitled Cyclopentane Heptan(ene)oic Add, 2-Heteroarylalkenyl Derivatives as Therapeutic Agents and was filed on May 18, 1995.

The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I

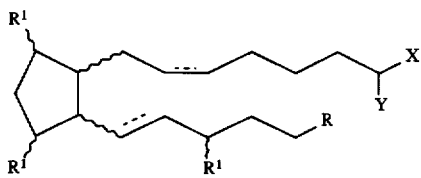

wherein the wavy segments represent an α or β bond, dashed lines represent a double bond or a single bond. R is a heteroaryl radical or a substituted heteroaryl radical. $R^1$ is hydroxyl or a hydrocarbyloxy or heteroatom sustituted hydrocarbyloxy comprising up to 20, e.g. up to 10 carbon atoms, and preferably a lower alkyloxy radical having up to six carbon atoms. X is selected from the group consisting of —$OR^6$ and —$N(R^6)_2$, wherein $R^6$ is hydrogen or a lower alkyl radical having from 1 to 6 carbon atoms and Y is =O or represents 2 hydrogen radicals and further provided that at least one of $R^1$ is a hydrocarbyloxy or heteroatom substituted hydrocarbyloxy.

In particular, the substituents on the heteroaryl radical may be selected from the group consisting of lower alkyl, e.g. $C_1$ to $C_6$ alkyl; halogen, e.g. fluoro, chloro, iodo and bromo; trifluoromethyl ($CF_3$); $COR^7$, e.g. $COCH_3$; $COCF_3$; $SO_2NR^7$, $SO_2NH_2$; $NO_2$; CN; etc., wherein $R^7$ is a lower alkyl radical having from 1 to 6 carbon atoms.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising

4 a container adapted to dispense its contents in a metered form; and an ophthalmic solution therein, as hereinabove defined.

A further aspect of the present invention provides methods of treating cardiovascular, pulmonary-respiratory, gastrointestinal, productive, allergic disease, shock and ocular hypertension which comprises administering an effective amount of a compound represented by the formula I.

Finally, certain of the compounds represented by the above formula, disclosed below and utilized in the methods of the present invention are novel and unobvious.

BRIEF DESCRIPTION OF THE DRAWING FIGURES

FIG. 2 is a schematic of the chemical synthesis of certain 1-amido compounds specifically disclosed as Examples 6(b)–(g) below.

FIG. 3 is a schematic of the chemical synthesis of certain 1-isopropyl ester compounds specifically disclosed as Examples 7(f)–(i), below.

FIG. 4 is a schematic of the chemical synthesis of certain 15-methoxy-substituted carboxylic acid compounds and isopropyl derivatives thereof.

DETAILED DESCRIPTION OF THE INVENTION

Figure 1:
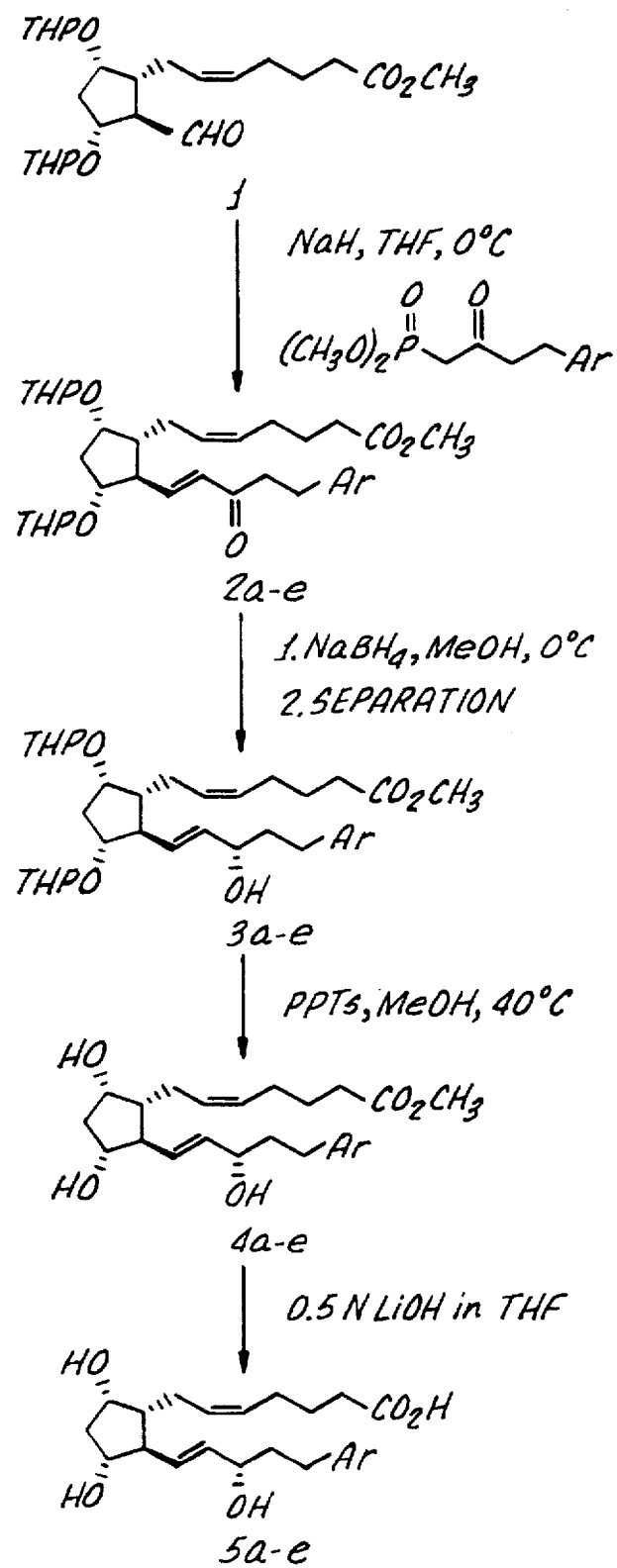
FIG. 1 is a schematic of the chemical synthesis of certain 1-carboxylic acid compounds and ester derivatives thereof specifically disclosed as Example 4(a)–(c) and 5(a)–(e) below.

The present invention relates to the use of cyclopentane heptan(ene)oic acid, 2-heteroaryl alkyl or alkenyl derivatives as therapeutic agents, e.g. as ocular hypotensives. The compounds used in accordance with the present invention are encompassed by the following structural formula I:

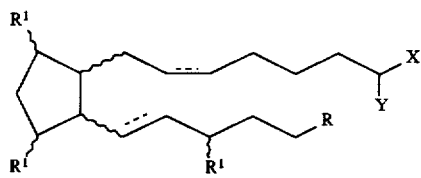

wherein the substituents and symbols are as hereinabove defined.

Preferably, the compounds used in accordance with the present invention have the following structural formula II:

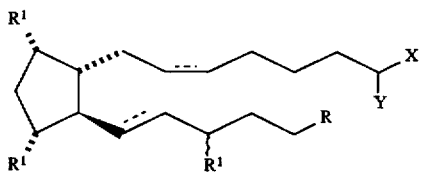

wherein the hatched segments represent α bonds, the solid triangle represents a β bond and the substituents and symbols are as hereinabove defined. The dotted lines on bonds between carbons 5 and 6 (C-5) and carbons 13 and 14 (C-13) indicate a single or double bond. If two solid lines are used at C-5, or C-13, it indicates a specific configuration for that double bond. Hatched lines used at position C-8, C-9 and C-11 indicate the α configuration. A triangle at position C-12 represents β orientation. A more preferred group of the compounds of the present invention includes compounds that have the following structural formula III:

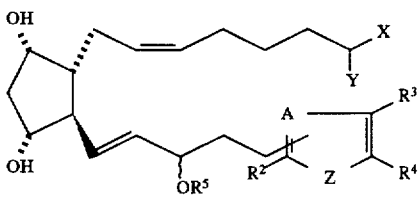

wherein Z is selected from the group consisting of O and S. A is selected from the group consisting of N, —CH, and C. $R^2$ is selected from the group consisting of hydrogen, halogen, and lower alkyl having from 1 to 6 carbon atoms, $R^3$ and $R^4$ are selected from the group consisting of hydrogen, halogen, lower alkyl having from 1 to 6 carbon atoms, or, together with

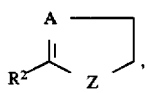

$R^3$ and $R^4$ forms a condensed aryl ring and $R^5$ is a lower alkyl having from 1 to 6 carbon atoms. Preferably, when X is —N($R^6$)$_2$, Y is =O.

More preferably, $R^5$ is methyl and at least one of $R^2$, $R^3$ or $R^4$ are independently selected from the group consisting of chloro, bromo and lower alkyl. In one aspect of the invention, at least one of $R^2$, $R^3$ or $R^4$ is chloro or bromo, and more preferably at least one of $R^2$, $R^3$ or $R^4$ is bromo or at least two of $R^2$, $R^3$ or $R^4$ are chloro or bromo. In another aspect of this invention, at least one of $R^2$, $R^3$ or $R^4$ is ethyl, propyl, or butyl.

Another preferred group includes compounds having the formula IV:

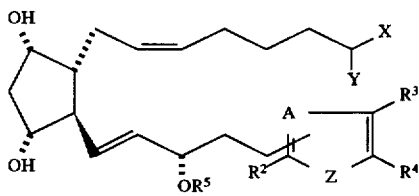

The above compounds of the present invention may be prepared by methods that are known in the art or according to the working examples below. The compounds, below, are especially preferred representative of the compounds of the present invention.

7-[3α,5α-Dihydroxy-2-(3α-methoxy-5-(3-(2-methyl)thienyl-1E-pentenyl)cyclopentyl]-5Z-heptenoic acid 7-[3α,5α-Dihydroxy-2-(3α-methoxy-5-(2-furanyl)-1E-pentenyl)cyclopentyl]-5Z-heptenoic acid.

Isopropyl 7-[3α,5α-Dihydroxy-2-(3α-methoxy-5-(2-furanyl)-1E-pentenyl)cyclopentyl]-5Z-heptenoate.

A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples, which are summarized in the reaction schemes of FIGS. 1 through 4, wherein the compounds are identified by the same designator in both the Examples and the Figures.

Compound 5a

7-[3α,5α,-Dihydroxy-2-(3α-hydroxy-5-(2-(3-chloro) benzothienyl-1E -pentenyl)cyclopentyl]-5Z-heptenoic acid

Step 1: Preparation of Enone 2a

To a suspension of sodium hydride (27 mg, 1.15 mmol) in tetrahydrofuran (THF) (2.0 mL) cooled to 0° C. was added dimethyl 4-(2-(3-chloro) benzothienyl)-2-oxo-butylphosphonate(363 mg, 1.15 mmol) in THF (2.2 mL). (In this Example, benzothienyl is an example of the hetero aryl radicals represented by R in the disclosure and claims and Ar in the Figures.) After 0.25 h a solution of the aldehyde 1 (507 mg, 1.04 mmol) in THF (2.0 mL) was added and the reaction was allowed to slowly warm to 23° C. over a period of 8 h. (In FIG. 1 THP represents tetrahydropyranyl.) The reaction solution was quenched with saturated aqueous $NH_4Cl$ and extracted with ethyl acetate (EtOAc.) The aqueous phase was made slightly acidic and extracted again with EtOAc. The combined organics were washed with brine, dried over $MgSO_4$, filtered and concentrated in vacuo. Flash column chromatography (silica gel, 2:1 hexane/EtOAc) gave 729 mg of enone 2a.

Step 2: Preparation of alcohol 3a

Sodium tetrahydridoborate (40 mg, 1.05 mmol) was added to a solution of the enone (729 mg, 1.05 mmol) in methanol (MeOH)(2.1 mL) at 0° C. After 2 h the solvent was removed in vacuo and the residue was stirred with 1N NaOH and EtOAc for 0.5 h. The organic portion was separated, dried over $MgSO_4$, filtered and concentrated in vacuo. The α-alcohol 3a was separated by flash column chromatography or HPLC (silica gel, 3:1 hexane/EtOAc).

Step 3: Preparation of Triol 4a:

A solution of the alcohol 3a and pyridinium p-toluene sulfonate (PPTs) (53 mg, 0.212 mmol) in MeOH (0.4 mL) was heated at 40° C. for 4 h. The solvent was removed in vacuo and the residue was diluted with EtOAc and then washed with 1N HCl, saturated aqueous $NaHCO_3$ and brine. The organic portion was dried over $MgSO_4$, filtered and concentrated in vacuo the triol 4a.

Step 4: Preparation of Carboxlic Acid 5a

The triol 4a was diluted with THF (0.8 mL) and lithium hydroxide (0.4 mL of a 0.5N solution in $H_2O$, 0.186 mmol) was added. After 16 h the reaction was acidified with 1N HCl and extracted with EtOAc. The organic portion was washed with brine, dried over $MgSO_4$, and concentrated in vacuo. The residue was purified by flash column chromatography (silica gel, 9:1 EtOAc/MeOH) to give 14.0 mg of free acid 5a.

By methods described for compound 5a, steps 1 through 4, the following compounds were prepared as illustrated in Scheme 1:

Compound 5b

7-[3α,5α-Dihydroxy-2-(3α-hydroxy-5-(5-(2,3-dibromo)thienyl)-1E-pentenyl)cyclopentyl]-5Z-heptenoic acid Prepared according to the procedures described above for 5a except the use of dimethyl 4-(5-(2,3-dibromo)thienyl)-2-oxo-butylphosphonate afforded 45 mg of free acid 5b.

Compound 5c

7-[3α,5α-Dihydroxy-2-(3α-hydroxy-5-(2-methyl) furanyl-1E-pentenyl)cyclopentyl]-5Z-heptenoic acid.

Prepared according to the procedures described above for 5a except the use of dimethyl 4-(5-(2-methyl)furanyl)-2-oxo-butylphosphonate afforded 63.6 mg of free acid 5c.

Compound 5d

7-[3α,5α-Dihydroxy-2-(3α-hydroxy-5-(3-(2,5-dibromo)thienyl)-1E-pentenyl)cyclopentyl]-5Z-heptenoic acid Prepared according to the procedures described above for 5a except the use of dimethyl 4-(3-(2,5-dibromo)thienyl)-2-oxo-butylphosphonate afforded 74 mg of free acid 5d.

Compound 5e

7-[3α,5α-Dihydroxy-2(3α-hydroxy-5-)5-(2-bromo-3-methyl)thienyl)-1E-pentenyl)cyclopentyl]-5Z-heptenoic acid Prepared according to the procedures described above for 5a except the use of dimethyl 4-(5-(2-bromo-3-methyl) thienyl)-2-oxobutylphosphonate afforded 40.6 mg of free acid 5e.

Synthesis of amides 6b-g (Scheme 2)

Compound 6b

7-[3α,5α-Dihydroxy-2-(3α-hydroxy-5-(5-(2,3-dibromo)thienyl)-1E-pentenyl)cyclopentyl]-5Z-heptenamide The 3α-triol 4b (27 mg, 0.048 mmol) isolated from step 3 during synthesis of 5b, was placed in a tube with ammonium chloride (76 mg, 1.42 mmol). Ammonia gas ~4.5 mL was condensed into the tube at −70° C. The tube was sealed and heated to 65° C. for 16 h. The tube was cooled to −70° C., vented and the ammonia allowed to evaporate on its own accord. The residue was dissolved in 1:1 $EtOAc/H_2O$. The organic portion was separated, dried over $MgSO_4$, filtered and concentrated in vacuo. Flash column chromatography (silica gel, 9:1 $CH_2Cl_2/MeOH$) gave 16.8 mg of the title compound 6b.

Compound 6c

7-[3α,5α-Dihydroxy-2-(3α-hydroxy-5-(5-(2-methyl) furanyl)-1E-pentenyl)cyclopentyl]-5Z-heptenamide According to the procedures described above for preparation of 6b the 3α-triol 4c (51 mg, 0.126 mmol) was converted to 25.1 mg of the title compound 6c.

Compound 6d

7-[3α,5α-Dihydroxy-2-(3α-hydroxy-5-(3-(2,5-dibromo)thienyl)-1E-pentenyl)cyclopentyl]-5Z-heptenamide According to the procedures described above for the preparation of 6b the 3α-triol 4d (24 mg, 0.42 mmol) was coverted to 12 mg of the title compound 6d.

Compound 6e

7-[3α,5α-Dihydroxy-2-(3α-hydroxy-5-(5-(2-bromo-3-methyl)thienyl)-1E-pentenyl)cyclopentyl]-5Z-heptenamide According to the procedures described above for the preparation of 6b the 3α-triol 4e (63 mg, 0.126 mmol) was converted to 33 mg of the title compound 6e.

Compound 6f

7-[3α,5α-Dihydroxy-2-(3α-hydroxy-5-(2-furanyl)-1E-pentenyl)cyclopentyl]-5Z-heptenamide According to the procedures described above for the preparation of 6b Methyl 7-[3α,5α-Dihydroxy-2-(3α-hydroxy-5-(2-furanyl)-1E-pentenyl)cyclopentyl]-5Z-heptenoate 4f (50 mg, 0.127 mmol) was coverted to 12 mg of the title compound 6f.

Compound 6g

7-[3α,5α-Dihydroxy-2-(3α-hydroxy-5-(4-(2-methyl)thienyl)-1E-pentenyl)cyclopentyl]-5Z-heptenamide According to the procedures described above for preparation of 6b Methyl 7-[3α,5α-Dihydroxy-2-(3α-hydroxy-5-(4-(2-methyl)thienyl)-1E-pentenyl)cyclopentyl]-5Z-heptenoate 4 g (65 mg, 0.154 mmol) was converted to 35.8 mg of the title compound 6g.

The isopropyl esters 7f–i were prepared as illustrated in Scheme 3 from the corresponding carboxylic acids 5f–i, which were prepared in an analogous manner to carboxylic acids 5a–e:

Compound 7f

Isopropyl 7-[3α,5α-Dihydroxy-2-(3α-hydroxy-5-(2-furanyl)-1E-pentenyl)cyclopentyl]-5Z-heptenoate A solution of the previously prepared carboxylic acid 5f (11.0 mg, 0.029 mmol) and O-isopropyl-N,N'-diisopropylisourea (270 mg, 1.45 mmol) in benzene (1.5 mL) was heated to 75° C. for 4 h. The reaction mixture was concentrated in vacuo and the residue was purified by flash column chromatography (silica gel, 100% EtOAc) to afford 3.7 mg of the title compound 7f.

Compound 7g

Isopropyl 7-[3α,5α-Dihydroxy-2-(3α-hydroxy-5-(4-(2-methyl)thienyl-1E-pentenyl) cyclopentyl]-5Z-heptenoate According to the procedures described above for the preparation of 7f the previously prepared carboxylic acid 5 g (10 mg, 0.025 mmol) was converted to 7.3 mg of the title compound 7g.

Compound 7h

Isopropyl 7-[3α,5α-Dihydroxy-2-(3α-hydroxy-5-(5-(2-methyl)thienyl)-1E-pentenyl)-cyclopentyl]-5Z-heptenoate According to the procedures described above for the preparation of 7f the previously prepared carboxylic acid 5h (10 mg, 0.025 mmol) was converted to 7.8 mg of the title compound 7h.

Compound 7i

Isopropyl 7-[3α,5α-Dihydroxy-2-(3α-hydroxy-5-(3-(2-methyl)thienyl)-1E-pentenyl)-cyclopentyl]-5Z-heptenoate According to the procedures described above for the preparation of 7f the 7-[3α,5α-Dihydroxy-2-(3α-hydroxy-5-(3-(2-methyl)thienyl)-1E-pentenyl)-cyclopentyl]-5Z-heptenoic acid 5i (10 mg, 0.025 mmol) was converted to 7.0 mg of the title compound 7i.

Compound 11f

7-[3α,5α-Dihydroxy-2-(3α-methoxy-5-(2-furanyl)-1E-pentenyl)cyclopentyl]-5Z-heptenoic acid

Step 1: Methylation of C-15 Hydroxyl Group

Methyl triflate (MeOTF) (97 mL, 0.86 mmol) was added to a solution of the mixture of alcohols 8f (160 mg, 0.28 mmol) and 2,6-di-t-butyl-pyridine (0.22 mL, 1.00 mmol) in $CH_2Cl_2$ (1.5 mL) at 0° C. The reaction was then allowed to warm to room tempeature and stirring was continued for 16 h. After quenching with saturated aqueous $NaHCO_3$ the reaction was extracted with EtOAc. The organic portion was washed with 1N HCl, brine, dried over $MgSO_4$, filtered and concentrated in vacuo. Flash column chromatography (silica gel, 4:1 hexane/EtOAc) provided 123 mg of the mixture of 15α, β-methyl ethers 9f.

Step 2: Removal of the Bis-Tetrahydropyranyl Protecting Groups

A solution of alcohols 9f (123 mg, 0.214 mmol) and pyridinium p-toluenesulfonate (40 mg, 0.16 mmol) in MeOH (3.0 mL) was heated at 40° C. for 4 h. The solvent was removed in vacuo. The residue was diluted with EtOAc and then washed with 1N HCl, saturated aqueous $NaHCO_3$ and brine. The organic portion was dried over $MgSO_4$, filtered and concentrated in vacuo. Purification of the residue by flash column chromatography (silica gel, 1:1 hexane/EtOAc followed by 100% EtOAc) gave 20.6 mg of 15α-methyl ether 10f.

Step 4: Preparation Carboxylic Acid 11f

The ester of 10f (10 mg, 0.025 mmol) was diluted with THF (0.4 mL) and lithium hydroxide (0.2 mL of a 0.5N solution in $H_2O$, 0.05 mmol) was added. After 16 h the reaction was acidified with 1N HCl and extracted with EtOAc. The organic portion was washed with brine, dried over $MgSO_4$, and concentrated in vacuo. The residue was purified by flash column chromatography (silica gel, 9:1 MeOH/EtOAc) to furnish 5.0 mg of the carboxylic acid 11f.

Compound 11i

7-[3α,5α-Dihydroxy-2-(3α-methoxy-5-(3-(2-methyl)thienyl)-1E-pentenyl) cyclopentyl]-5Z-heptenoic acid According to the procedures described above for the preparation of 11f the mixture of alcohols 8i (295 mg, 0.50 mmol) were converted to 9.4 mg of title compound 11i.

Compound 12f

Isopropyl 7-[3α,5α-Dihydroxy-2-(3α-methoxy-5-(2-furanyl)-1E-pentenyl)cyclopentyl]-5Z-heptenote 12f A mixture of ester 10f (20 mg, 0.05 mmol) and potassium carbonate (20.4 mg, 0.15 mmol) in anHydrous isopropanol (3.0 mL) was heated at 100° C. for 16 h. The reaction was concentrated in vacuo and the residue as stirred with 1:1 EtOAc/$H_2O$ (~20 mL) for 0.5 h. The organic portion was separated, dried over $MgSO_4$, filtered and concentrated in vacuo. Purification of the residue by flash column chromatography (silica gel, 2:1 hexane/EtOAc) provided 20.2 mg of the title compound 12f.

Certain of the above compounds were tested for activity in the various in vitro assays described below and the results are reported in Tables 1 and 2, below.

Activity at different prostanoid receptors was measured in vitro in isolated smooth muscle preparations. FP-activity was measured as contraction of the isolated feline iris sphincter. $EP_4$-activity was measured as relaxation of smooth muscle of isolated rabbit jugular vein. TP-vasoconstrictor activity was measured as contraction of rings of the isolated rat thoracic aorta. Effects on platelets from healthy human donors were measured by incubating platelet-rich plasma with the compounds described herein. Inhibition of aggregation was determined by the ability of the compounds described herein to inhibit platelet aggregation in platelet-rich plasma induced by 20 μM adenosine diphosphate (ADP).

Potential therapeutic applications of the compounds described above are in osteoporosis, constipation, renal disorders, sexual dysfunction, baldness, diabetes, cancer and in disorder of immune regulation.

Many examples also have pronounced activity at the FP receptor, provisionally termed $FP_{VASC}$ associated with the vascular endothelium in the rabbit jugular vein preparation. Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension.

The effects of certain of the compounds of the working examples on intraocular pressure are also provided in the following tables. The compounds were prepared at the said concentrations in a vehicle comprising 0.1% polysorbate 80 and 10 mM tris (hydroxy methyl) aminomethane hydrochloride (TRIS) base. Dogs were treated by administering 25 μl to the ocular surface, the contralateral eye received vehicle as a control. Intraocular pressure was measured by applanation pneumatonometry. Dog intraocular pressure was measured immediately before drug administration and at 6 hours thereafter.

TABLE 1

| AGN-# | FP | $EC_{50}$ (nM) EP$_1$ | EP$_3$ | DP/EP$_2$ | $IC_{25}$ EP$_4$ | FP/EP$_4$ Ratio | TP | Platelets aggreg | Platelets inhib | Dog IOP (1 day) | Hyp/ Miosis |
|---|---|---|---|---|---|---|---|---|---|---|---|
| 5a | 568 | | | | 21190 | 0.03 | | | | | |
| 5b | 0.8 | | | | 23 | 0.03 | 692 | | | | |
| 5c | 24 | | | | 23 | 1.0 | >10$^4$ | | | 0.1%/−2.7 | 1.13/ pinpoint |
| 5d | 0.25 | | | | | | | | | | |

TABLE 1-continued

| AGN-# | EC$_{50}$ (nM) FP | EP$_1$ | EP$_3$ | DP/EP$_2$ | IC$_{25}$ EP$_4$ | FP/EP$_4$ Ratio | TP | Platelets aggreg | inhib | Dog IOP (1 day) | Hyp/ Miosis |
|---|---|---|---|---|---|---|---|---|---|---|---|
| 5e | 1.4 | | | | | | | | | | |
| 6b | 2.2 | | | | 165 | 0.01 | NA | | | | |
| 6c | 291 | | | | 3760 | 0.08 | | | | 0.1%/−2.1 | 0.75/ pinpoint |
| 6d | 0.44 | | | | | | | | | | |
| 6e | 50 | | | | | | | | | | |
| 6f | 35 | | | | 620 | 0.06 | NA | | | 0.1%/−4.4 0.01%/−3.2 | 1.0/ pinpoint 1.5/ pinpoint |

TABLE 2

| AGN-# | FP | EC$_{50}$ (nM) EP$_1$ | EP$_3$ | DP/EP$_2$ | IC$_{25}$ EP$_4$ | FP/EP$_4$ Ratio | TP | Platelets aggreg | inhib | Dog IOP (1 day) | Hyp/ Miosis |
|---|---|---|---|---|---|---|---|---|---|---|---|
| 6g | 33 | | | | 1630 | 0.02 | NA | | | 0.1%/ −3.6 | 0.6/ pinpoint |
| 7f | | | | | | | | | | | |
| 7g | | | | | | | | | | | |
| 7h | | | | | | | | | | | |
| 7i | | | | | | | | | | | |
| 11f | 4 | | | | 57 | 0.07 | | | | | |
| 11i | 5 | | | | 100 | 0.05 | | | | | |

TABLE 2-continued

| AGN-# | EC₅₀ (nM) | | | | IC₂₅ | FP/EP₄ | | Platelets | | Dog IOP | Hyp/ |
|---|---|---|---|---|---|---|---|---|---|---|---|
| | FP | EP₁ | EP₃ | DP/EP₂ | EP₄ | Ratio | TP | aggreg | inhib | (1 day) | Miosis |

12f

The compounds of the invention may also be useful in the treatment of various pathophysiological diseases including acute myocardial infarction, vascular thrombosis, hypertension, pulmonary hypertension, ischemic heart disease, congestive heat failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petrolatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules make of gelalin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, marmitol or sorbitol, cellulose preparations and/or calcium phosphates, for example tricalcium phosphate or calcium hydrogen phosphate, as well as inders such as starch, paste using for example, maize starch, wheat starch, rich starchy, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. For example, the present invention contemplates certain pro-drugs and derivatives of the above disclosed compounds, wherein $R^6$ is

These compounds may be made by methods known in the art, i.e. the acetylation of the 1-hydroxy or 1-amino or 1-amido derivatives, etc., disclosed above, with the appropriate acid chloride or acid anhydride. $R^6$ may be

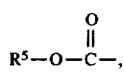

as well, when said 1-hydroxy, or 1-amino or 1-amido derivatives are reacted with the appropriate ortho ester. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

I claim:

1. A method of treating ocular hypertension or glaucoma which comprises topically administering to a mammal having ocular hypertension a therapeutically effective amount of a compound represented by formula I:

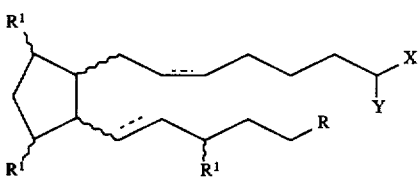

wherein wavy line attachments indicate either the alpha (α) or beta (β) configuration; dashed bonds represent a double bond or a single bond, R is a heteroaryl or a substituted heteroaryl radical, $R^1$ is hydroxyl or hydrocarbyloxy or hetero atom substituted hydrocarbyloxy comprising up to 20 carbon atoms, X is selected from the group consisting of —$OR^6$ and —$N(R^6)_2$ wherein $R^6$ is selected from the group consisting of hydrogen, a lower alkyl radical having from 1 to 6 carbon atoms,

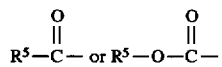

wherein $R^5$ is a lower alkyl radical having from 1 to 6 carbon atoms and Y is =O or represents 2 hydrogen radicals and further provided at least one of $R^1$ is a hydrocarbyloxy or an heteroatom substituted hydrocarbyloxy or a pharmaceutically-acceptable salt thereof.

2. The method of claim 1 wherein said compound is represented by formula II

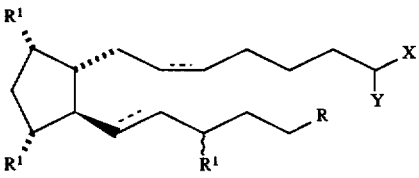

wherein the hatched segments represent α bonds and the solid triangle represents a β bond.

3. The method of claim 2 wherein the substituent on the heteroaryl radical is selected from the group consisting of lower alkyl, halogen, trifluoromethyl ($CF_3$), $COR_7$, $COCF_3$, $SO_2NR_7$, $SO_2NH_2$, $NO_2$ and CN, wherein $R^7$ is a lower alkyl radical.

4. The method of claim 2 wherein said compound is represented by formula III:

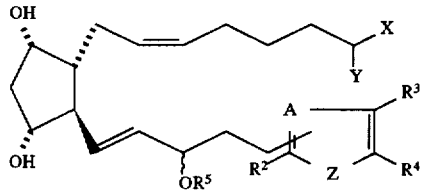

wherein Z is selected from the group consisting of O and S, A is selected from the group consisting of N, —CH, and C, $R^2$ is selected from the group consisting of hydrogen, halogen and lower alkyl having from 1 to 6 carbon atoms, $R^3$ and $R^4$ are selected from the group consisting of hydrogen, halogen, lower alkyl having from 1 to 6 carbon atoms, or, together with

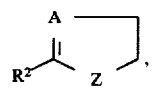

$R^3$ and $R^4$ forms a condensed aryl ring and $R^5$ is a lower alkyl having from 1 to 6 carbon atoms.

5. The method of claim 4 wherein said compound is represented by formula IV:

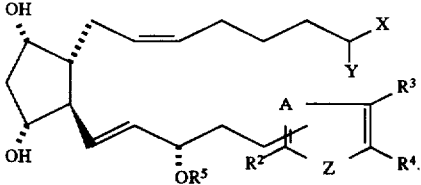

6. The method of claim 5 wherein X is —OH or —$NH_2$.

7. The method of claim 5 wherein Y is =O and X is —OH.

8. The method of claim 5 wherein Y is =O and X is isopropoxy.

9. The method of claim 5 wherein Z is S.

10. The method of claim 5 wherein Z is O.

11. The method of claim 9 wherein said compound is 7-[3α,5α-Dihydroxy-2-(3α-methoxy-5-(3-(2-methyl)thienyl)-1E-pentenyl)cyclopentyl]-5Z-heptenoic acid.

12. The method of claim 10 wherein said compound is 7-[3α,5α-Dihydroxy-2-(3α-methoxy-5-(2-furanyl)-1E-pentenyl)cyclopentyl]-5Z-heptenoic acid.

13. The method of claim 10 wherein said compound is Isopropyl 7-[3α,5α-Dihydroxy-2-(3α-methoxy-5-(2-furanyl)-1E-pentenyl)cyclopentyl]-5Z-heptenoate.

* * * * *

UNITED STATES PATENT AND TRADEMARK OFFICE
CERTIFICATE OF CORRECTION

PATENT NO. : 5,741,810
DATED : April 21, 1998
INVENTOR(S) : Burk

It is certified that error appears in the above-indentified patent and that said Letters Patent is hereby corrected as shown below:

In the drawings:

Fig. 3, Sheet 2 of 3, Scheme 3, after first formula add --5f-i--

Fig. 3, Sheet 2 of 3, Scheme 3, after third formula add --7f-i--

Fig. 4, Sheet 3 of 3, Scheme 4, fourth formula, delete "11f" and insert in place thereof --11f,i--

Column 3, line 18; delete "Adds" and insert in place thereof --Acid--

Column 10, line 62; delete "anHydrous" and insert in place thereof --anhydrous--

Column 17, line 20; delete "heat" and insert in place thereof --heart--

Column 17, line 43; delete "make" and insert in place thereof --made--

Column 17, line 43; delete "gelalin" and insert in place thereof --gelatin--

Column 17, line 63; delete "Marmitol" and insert in place thereof --mannitol--

Column 18, line 36; delete "tables" and insert in place thereof --tablets--

Signed and Sealed this

Eighth Day of September, 1998

*Attest:*

BRUCE LEHMAN

*Attesting Officer*  *Commissioner of Patents and Trademarks*